(12) United States Patent
Hendriks et al.

(10) Patent No.: US 10,390,805 B2
(45) Date of Patent: Aug. 27, 2019

(54) BIOPSY NEEDLE WITH LARGE FIBER DISTANCE AT THE TIP

(71) Applicant: KONINKLIJKE PHILIPS N.V., Eindhoven (NL)

(72) Inventors: Bernardus Hendrikus Wilhelmus Hendriks, Eindhoven (NL); Waltherus Cornelis Jozef Bierhoff, Veldhoven (NL); Christian Reich, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 889 days.

(21) Appl. No.: 14/406,534

(22) PCT Filed: Jun. 17, 2013

(86) PCT No.: PCT/IB2013/054957
§ 371 (c)(1),
(2) Date: Dec. 9, 2014

(87) PCT Pub. No.: WO2014/001953
PCT Pub. Date: Jan. 3, 2014

(65) Prior Publication Data
US 2015/0182206 A1    Jul. 2, 2015

Related U.S. Application Data

(60) Provisional application No. 61/664,226, filed on Jun. 26, 2012.

(51) Int. Cl.
*A61B 10/04*    (2006.01)
*A61B 1/06*    (2006.01)
(Continued)

(52) U.S. Cl.
CPC ............ *A61B 10/04* (2013.01); *A61B 1/0646* (2013.01); *A61B 1/0684* (2013.01); *A61B 1/07* (2013.01);
(Continued)

(58) Field of Classification Search
CPC ... A61B 10/0275; A61B 10/04; A61B 1/0646; A61B 1/0684; A61B 1/07;
(Continued)

(56) References Cited

U.S. PATENT DOCUMENTS 5,526,112 A    6/1996  Sahagen
5,769,791 A    6/1998  Benaron et al.
(Continued)

FOREIGN PATENT DOCUMENTS

CN    87213746 U    9/1988
CN    2899710 Y    5/2007
(Continued)

OTHER PUBLICATIONS

Nachabe, R. et al., "Estimation of lipid and water concentrations in scattering media with diffuse optical spectroscopy from 900 to 1600nm", J. Biomed. Opt 15, 037015(2010).
(Continued)

*Primary Examiner* — Michael T Rozanski (57) ABSTRACT

A biopsy device is provided having a shaft and a tubular member. The shaft may be movably accommodated within the tubular member and may have a longitudinal axis and a distal end with a bevel. At least two channels are formed within the shaft in a longitudinal direction of the shaft, each channel forming an opening in the bevel surface, wherein an optical fiber is accommodated within each of the channels. Furthermore, a recess for accommodating tissue to be
(Continued)

extracted may be formed in the shaft adjacent the distal end of the shaft. The bevel is facing upwardly whereas the recess is facing sidewardly.

17 Claims, 6 Drawing Sheets

(51) Int. Cl.
  *A61B 1/07* (2006.01)
  *A61B 5/00* (2006.01)
  *A61B 10/02* (2006.01)
  *A61B 90/13* (2016.01)
  *A61B 90/11* (2016.01)

(52) U.S. Cl.
  CPC .......... *A61B 5/0073* (2013.01); *A61B 5/0075* (2013.01); *A61B 5/0084* (2013.01); *A61B 5/6848* (2013.01); *A61B 5/742* (2013.01); *A61B 5/7475* (2013.01); *A61B 10/0275* (2013.01); *A61B 90/11* (2016.02); *A61B 90/13* (2016.02); *A61B 2010/045* (2013.01); *A61B 2576/00* (2013.01)

(58) Field of Classification Search
  CPC .......... A61B 2010/045; A61B 2576/00; A61B 5/0073; A61B 5/0075; A61B 5/0084; A61B 5/6848; A61B 5/742; A61B 5/7475; A61B 90/11; A61B 90/13
  See application file for complete search history.

(56) References Cited

U.S. PATENT DOCUMENTS

| | | |
|---|---|---|
| 6,258,071 B1 | 7/2001 | Brookes |
| 7,787,129 B2 | 8/2010 | Zysk et al. |
| 8,231,544 B2 | 7/2012 | Mark |
| 2002/0128570 A1 | 9/2002 | Bowman et al. |
| 2005/0203419 A1 | 9/2005 | Ramanujam et al. |
| 2010/0317964 A1 | 12/2010 | Hendriks |
| 2011/0218445 A1 | 9/2011 | Braun et al. |
| 2011/0251494 A1 | 10/2011 | Hendriks et al. |
| 2012/0029360 A1 | 2/2012 | Hendriks et al. |

FOREIGN PATENT DOCUMENTS

| | | |
|---|---|---|
| CN | 101779947 A | 7/2010 |
| JP | H0310255 A | 1/1991 |
| RU | 50799 U1 | 1/2006 |
| WO | 2010119392 A1 | 10/2010 |

OTHER PUBLICATIONS

Farrell, T.J. et al., "A diffusion theory model of spatially resolved, steady-state diffuse reflectance for the non-invasive determination of tissue optical properties in vivo", Med. Phys. 19 (1992) p. 879-888.

Nachabe, R. et al., "Estimation of biological chromophores using diffuse optical spectroscopy: benefit of extending the UV-VIS wavelength range to include 1000 to 1600 nm", Optics Express, vol. 18, 2010, pp. 1432-1442.

Official Action, Jun. 6, 2017, Russian Patent Application No. 2015102162 (with translation).

BIOPSY NEEDLE WITH LARGE FIBER DISTANCE AT THE TIP

CROSS-REFERENCE TO PRIOR APPLICATIONS

This application is the U.S. National Phase application under 35 U.S.C. § 371 of International Application Serial No. PCT/IB2013/054957, filed on Jun. 17, 2013, which claims the benefit of U.S. Application Ser. No. 61/664,226, filed on Jun. 26, 2012. These applications are hereby incorporated by reference herein.

FIELD OF THE INVENTION

The invention generally relates to a needle with integrated fibers. Particularly, the invention relates to a biopsy needle with lateral recess for taking a biopsy and integrated fibers. Further, the invention relates to a system including such a needle, for tissue inspection based on diffuse reflectance and autofluorescence measurements to diagnose whether tissue is cancerous or not, before extracting tissue.

BACKGROUND OF THE INVENTION

Figure 1:
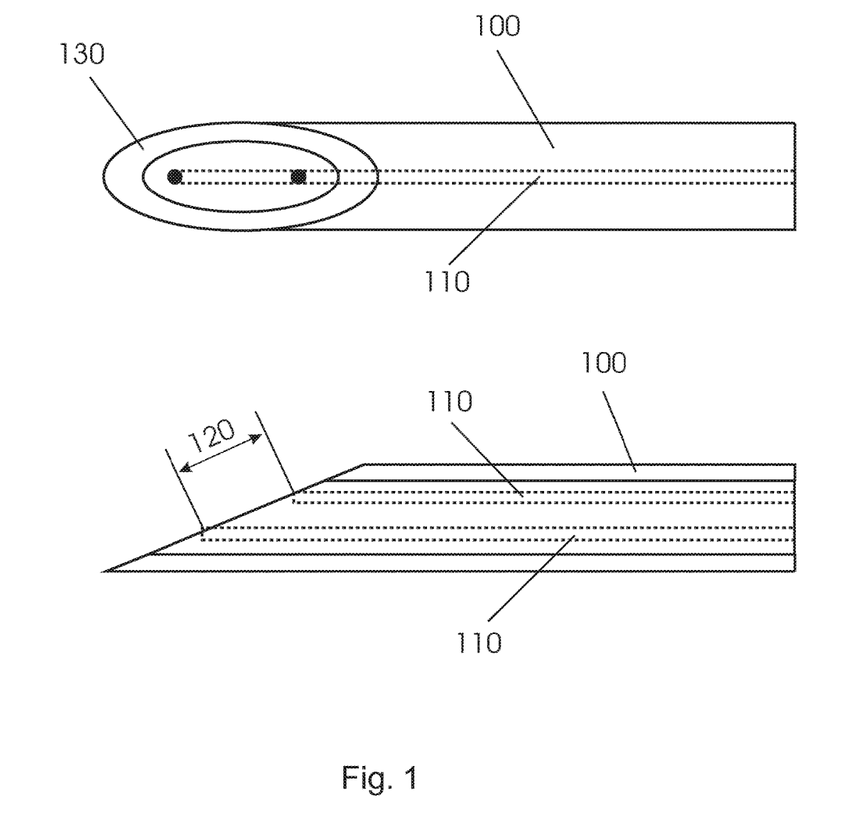
FIG. 1 is an illustration of a known needle including two optical fibers.

In order to position a biopsy needle under image guidance more accurately in the suspicious tissue, tissue sensing at the tip of the device is required. Current biopsy needle do not have such tissue feedback possibilities. Recently, elongated interventional devices like that shown in FIG. 1 have been reported with optical fibers 110 integrated into the device 100 allowing tissue feedback at the tip of the device. In order to allow tissue discrimination these devices employed diffuse reflectance spectroscopy. In order to sense chromophores in the tissue having low concentrations the fiber distance 120 between the source and detector fiber are designed to be as large as possible. In general a needle like device 100 has only limited diameter. In order to make the source-detector fiber distance large the fiber ends are positioned at the slanted surface of the tip of needle allowing fiber distances larger than the diameter of the needle.

Figure 2:
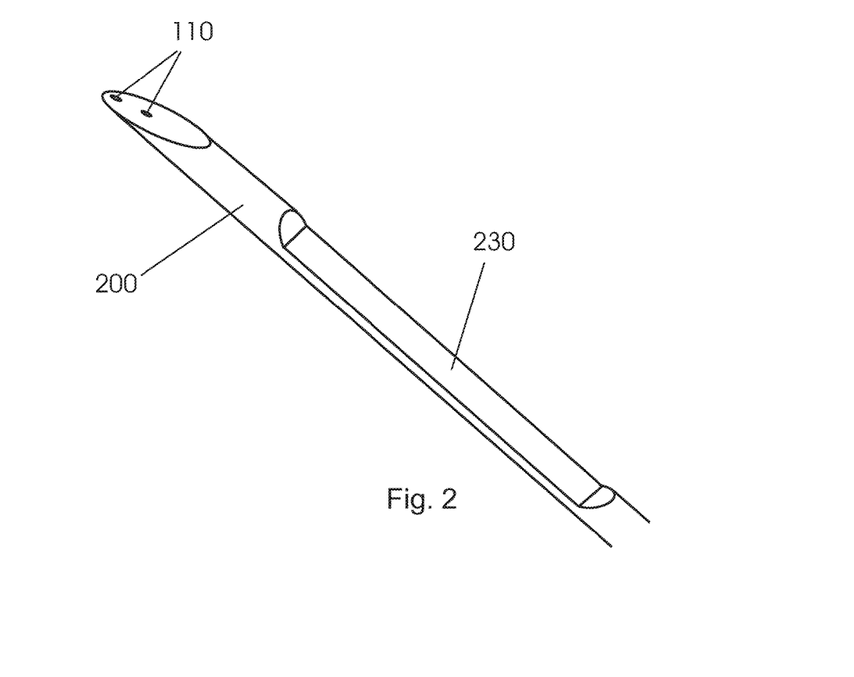
FIG. 2 is an isometric view of a known needle with notch.
Figure 3:
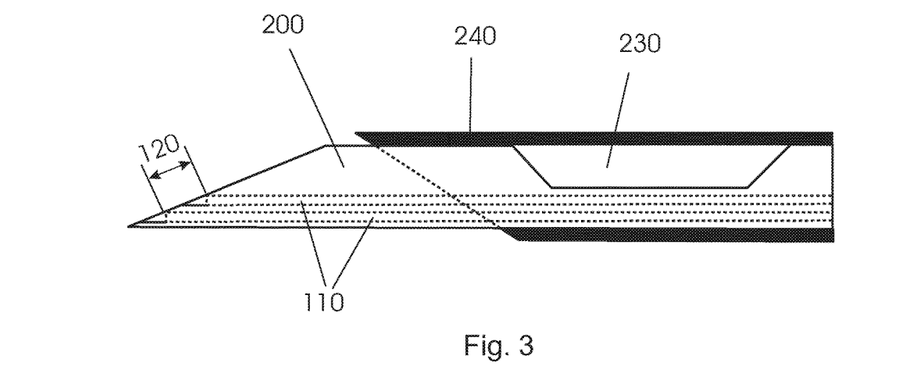
FIG. 3 is a side view of the needle of FIG. 2.

FIGS. 2 and 3 show different views of another conventional biopsy device 200 with a notch 230 at the circumference of the shaft and a tubular member 240 for selectively covering the notch. However, a large source-detector fiber distance cannot be realized when integrating fibers 110 into the device 200. The reason for this is the notch that is required in order to be able to take biopsies. As a result of this when integrating the fibers 110 into the biopsy device and since the fibers must not be in the notch of the biopsy needle the fiber distance 120 that can be achieved is only small.

SUMMARY OF THE INVENTION

An object of the invention is to provide a biopsy needle including a notch or recess for taking a biopsy, with improved facilities for tissue inspection. This and further objects are solved by the subject-matter of the independent claim. Further embodiments are described in the dependent claims.

Generally, a biopsy device according to an embodiment may comprise a solid shaft and a tubular member. The shaft may be movably accommodated within the tubular member and may have a longitudinal axis and a distal end with a bevel. At least two channels are formed within the shaft in a longitudinal direction of the shaft, each channel forming an opening in the bevel surface, wherein at least one optical fiber is accommodated within each of the channels. Furthermore, a recess for accommodating tissue to be extracted may be formed in the shaft adjacent the distal end of the shaft.

A 'bevel' is a geometrical structure allowing for introducing the needle into tissue. Usually, a shaft of a needle includes a circular cross section. The distal end of a needle shaft is cut such that an oval surface is formed, which is inclined relative to the longitudinal axis of the shaft. The bevel forms a pointed tip at the most distal end of the needle. It should be noted that the bevel might form an acute angle with the shaft, such that the needle includes a pointed tip. Preferably, the acute angle might be approximately 20°.

According to an embodiment, the bevel is facing upwardly whereas the recess is facing sidewardly.

In the following, geometrical aspects will be defined for a better understanding. First of all, the needle includes a longitudinal main axis, usually the centre axis of a rotationally symmetrical shaft. Further, the tip portion of the needle is cut at an angle to the main axis forming the bevel. Looking onto the surface of the bevel as well as on the shaft means looking from 'above'. Consequently, looking in the opposite direction means looking 'upwardly'. Accordingly, 'under' the needle is opposite to 'above'. The pointed tip of the bevel is directed to the 'front' of the needle. As a result, looking from the 'side', it is possible to recognize the angle between the bevel and the main axis, and further it is possible to look onto and into a recess formed at the side. Consequently, looking in the opposite direction means looking 'sidewardly'.

Although the bevel surface is not oriented parallel to the longitudinal axis of the shaft, i.e. a normal vector of the bevel surface is not oriented perpendicular to the longitudinal axis of the shaft, this surface shall be understood as facing upwardly. Correspondingly, although a normal vector of the lateral recess may be inclined, i.e. may define an angle between the directions upwardly and sidewardly, it shall be understood that the recess is facing sidewardly. In other words, as long as a vector component of the normal vector of the bevel is oriented perpendicular to the longitudinal axis of the shaft, the bevel shall be considered as facing upwardly. Correspondingly, as long as a vector component of the normal vector of the recess is oriented perpendicular to a plane including both the longitudinal axis of the shaft and the normal vector of the bevel, the recess shall be considered as facing sidewardly.

According to an embodiment, the recess in the shaft of the biopsy device is formed such that a normal vector of the recess is oriented relative to the plane including the shaft axis and the normal vector of the bevel at an angle of more than 30 degrees, preferably more than 45 degree and more preferably more than 70 degrees. In other words, the recess is located relative to the bevel with an offset in a circumferential direction of the shaft.

According to a further embodiment, the normal vector of the recess is oriented perpendicular relative to the plane with shaft axis and normal vector of the bevel.

According to an embodiment, the distance between the two openings in the bevel surface of the shaft of the biopsy device is greater than the diameter of the shaft.

In case of two fibers, wherein both fibers being capable of transmitting light, an end surface of one of the fibers might be located at a top of the bevel and the other one of the fibers might be located at a bottom of the bevel.

The wording 'top of the bevel' should indicate an area being part of the surface of the bevel, which area is located adjacent to the distal edge between the bevel and the shaft.

That is, a fiber which is located at the top of the bevel might be located at the oval surface of the bevel, near the distal edge, i.e. the pointed tip.

On the other hand, 'bottom of the bevel' means the area being part of the surface of the bevel, which area is located diametric to the top of the bevel. That is, the fiber which is located at the bottom of the bevel might be on or near or adjacent beside the long axis of the oval surface of the bevel near the proximal edge between bevel and shaft.

It should be noted that the end surface of a fiber at the opening in the bevel may have a circular shape or an oval shape in case of a substantially circular cross section of the fiber. Depending on the angle at which the fiber will end at the bevel surface, the shape of the end surface of the fiber will be effected and therefore also the direction of the emitted or received light.

The shaft of the needle has an outer diameter, and the end surfaces of the fibers are arranged at a distance to each other. Preferably, the distance between the fiber ends is greater than the diameter of the shaft. For example, the distance is more than 1.1 times greater than the diameter. Particularly, the distance may be more than 1.25 times greater than the diameter. Preferably, the distance may be more than 1.5 times greater than the diameter. In other words, the distance between the fiber ends at the tip part of the needle should be as great as possible. Such distances are measured from the central axis of one of the fibers to the central axis of the other one of the fibers.

According to a further embodiment, the shaft is movable between a first position in which the recess is covered by the tubular member and a second position in which the recess is not covered by the tubular member. The tubular member may include a sharpened distal edge.

According to another embodiment, the biopsy device further comprises a console including a light source, a light detector and a processing unit for processing the signals provided by the light detector, wherein one of the light source and the light detector may provide wavelength selectivity. The light source may be one of a laser, a light-emitting diode or a filtered light source, and the console may further comprise one of a fiber switch, a beam splitter or a dichroic beam combiner. Furthermore, the device may be adapted to perform at least one out of the group consisting of diffuse reflectance spectroscopy, diffuse optical tomography, differential path length spectroscopy, and Raman spectroscopy.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

Figure 4:
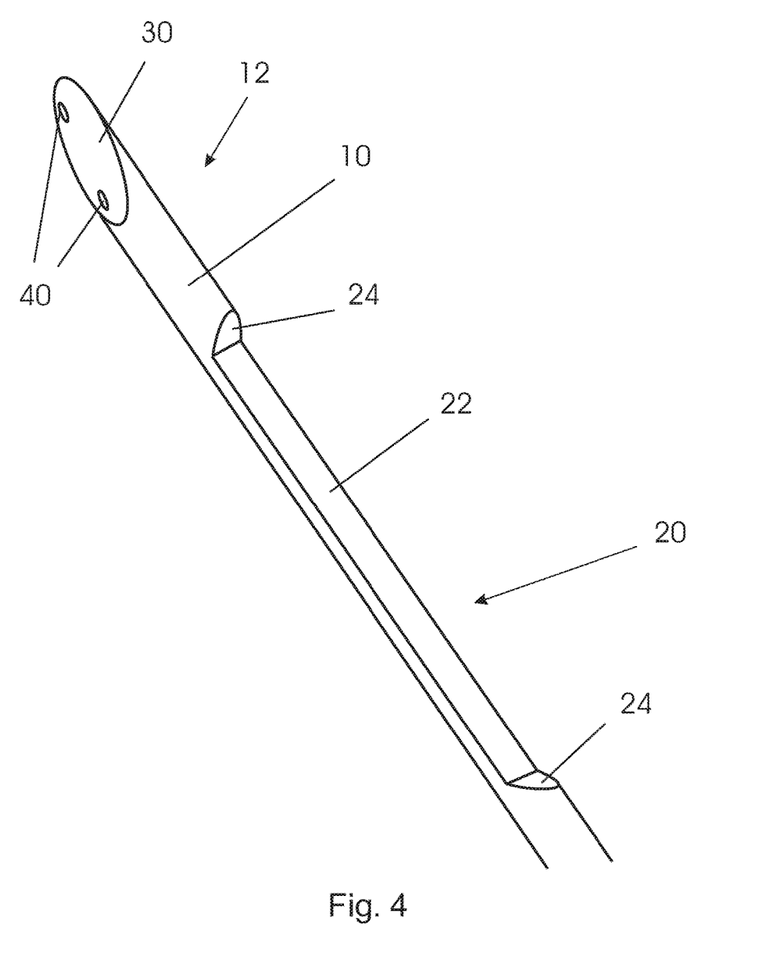
FIG. 4 is an isometric view of a biopsy needle with recess at the side.
Figure 5:
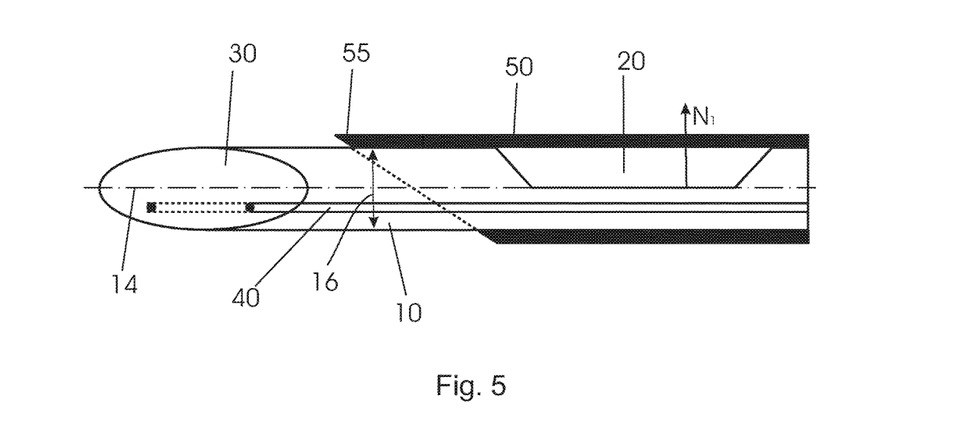
FIG. 5 is a view from above onto a needle with a recess at the side.
Figure 6:
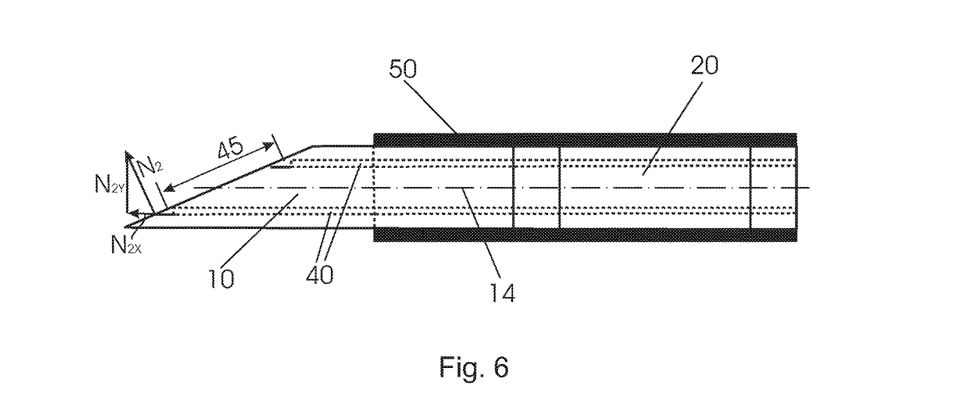
FIG. 6 is a side view of a needle with a recess at the side.

In FIGS. 4 to 6, an embodiment of a biopsy device is shown which comprises a shaft 10, a notch or recess 20 adjacent the distal end 15, a bevel 30 at the distal end 15, two optical fibers 40 accommodated in longitudinal direction within the shaft 10, and an outer tubular member 50 which is movable relative to the shaft.

As visualized in the isometric view of FIG. 4, the recess 20 is rotated in circumferential direction relative to the surface of the bevel 30, i.e. is formed relative to the bevel with an offset in a circumferential direction. The recess 20 comprises a flat bottom surface 22 and chamfers 24 at the respective ends of the bottom surface. It will be understood that the recess may also have any other suitable shape like for example a deepened bottom surface with elevated edges formed in longitudinal direction.

As shown in FIGS. 5 and 6, a tubular member 50 is sized such that the solid shaft 10 fit into the hollow tubular member 50 so as to be movably accommodated within the tubular member. In use, the tubular member 50 will be positioned relative to the shaft like it is shown in FIGS. 5 and 6, when the biopsy device is introduced into tissue. As soon as for example cancerous tissue is detected by means of spectroscopy utilizing the optical fibers 40, only the shaft 10 may be pushed forward until the recess 20 is not anymore covered by the tubular member 50. In this situation, soft tissue may enter the recess. Subsequently, the tubular member 50 can be pushed forward so as to cut the tissue by means of the sharpened distal edge 55 of the tubular member, so that a tissue sample may remain within the recess thus being safely enclosed to be extracted from the tissue by pulling the biopsy device out of the tissue.

Two channels are formed within the shaft in a longitudinal direction of the shaft for accommodating optical fibers 40. The channels and thus the optical fibers are arranged in the shaft material which remains beside the recess, as can be seen from a first direction, as in FIG. 5, and are arranged with a maximal distance from each other, as can be seen from a second direction, as in FIG. 6. As a result, the ends of the fibers 40 located at the surface of the bevel 30 may have a distance 45 from each other which may be larger than the diameter 16 of the shaft 10.

As shown in FIG. 5, the channels with optical fibers 40 may be provided with a lateral offset relative to the shaft axis 14. Particularly, the plane including both fiber channels may be arranged in parallel and with a non-zero-distance to the plane including the shaft axis and the normal vector of the bevel. By way of this, the recess 20 may have a maximum depth of approximately half the diameter of the shaft.

It is noted that the 'bevel' might also have another shape or structure at the tip of the needle, useful for introducing the needle into a tissue. For example, the bevel might be a convex or concave surface, or the bevel might be a combination of several small surfaces, wherein these surfaces are connected to each other by steps or edges. It might also be possible that the cross section of the shaft is not completely cut by the bevel, such that an area remains which is blunt, i.e. is for example perpendicularly orientated relative to the longitudinal axis of the shaft. Such a 'blunt' end might include rounded edges or might also form a rounded leading edge. As another example, a sharp edge might be formed by two or more slanted surfaces being symmetrically or asymmetrically arranged to form the tip of the needle.

As described above, the normal vector of the recess shall be at least inclined thus having a vector component perpendicular relative to a plane including the shaft axis and the normal vector of the bevel surface. In FIG. 5, a normal vector $N_1$ is shown, which vector is defined perpendicular to the flat bottom surface 22 of the recess 20. The vector $N_1$ in FIG. 5 is perpendicular to the plane including the shaft axis 14 and the normal vector $N_2$ of the bevel surface.

The normal vector $N_2$ is shown in FIG. 6, which vector is defined by the surface of the bevel 30. Further shown in FIG. 6 are vector components $N_{2x}$ and $N_{2y}$, with the vector component $N_{2x}$ extending parallel to the longitudinal shaft axis 14 and the vector component $N_{2y}$ extending perpendicular to the longitudinal shaft axis. It will be understood that also the normal vector $N_1$ may be divided in vector components, for example in an embodiment in which the normal vector of the recess is inclined relative to the plane including the shaft axis 14 and the normal vector $N_2$ of the bevel surface.

Figure 7:
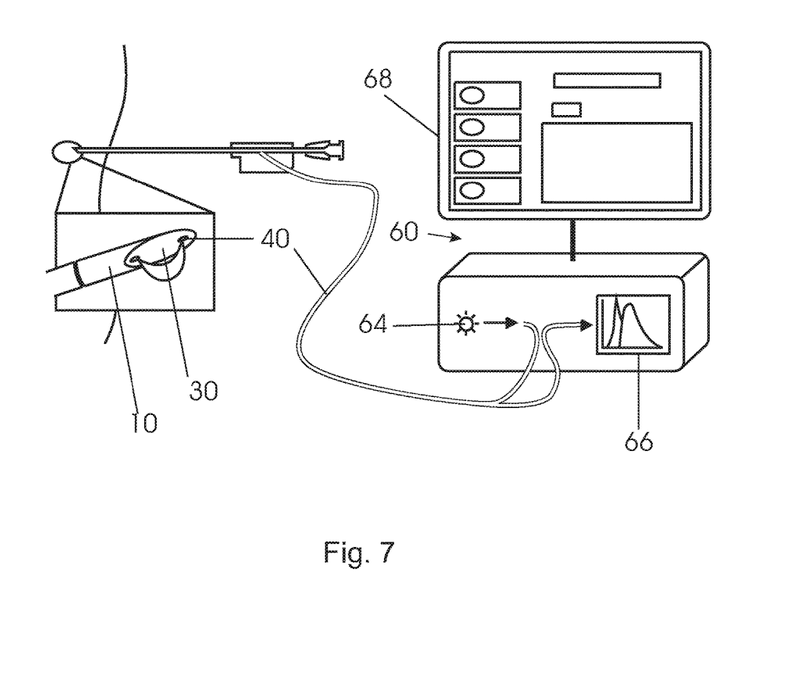
FIG. 7 shows a system including a needle and a console.

As shown in FIG. 7, the fibers 40 of the interventional device are connected to an optical console 60. The optical fibers can be understood as light guides or optical waveguides. In an embodiment, the console 60 comprises a light source 64 in the form of a halogen broadband light source with an embedded shutter, and an optical detector 66. The optical detector 66 can resolve light with a wavelength substantially in the visible and infrared regions of the wavelength spectrum, such as from 400 nm to 1700 nm. The combination of light source 64 and detector 66 allows for diffuse reflectance measurements. For a detailed discussion on diffuse reflectance measurements see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

On the other hand, also other optical methods can be envisioned like diffuse optical tomography by employing a plurality of optical fibers, differential path length spectroscopy, fluorescence and Raman spectroscopy to extract tissue properties.

A processor transforms the measured spectrum into physiological parameters that are indicative for the tissue state and a monitor 68 may be used to visualize the results.

A computer program executable on the processor may be provided on a suitable medium such as an optical storage medium or a solid-state medium supplied together with or as part of the processor, but may also be distributed in other forms, such as via the Internet or other wired or wireless telecommunication systems.

For fluorescence measurements the console must be capable of providing excitation light to at least one source fiber while detecting tissue-generated fluorescence through one or more detection fibers. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fiber as the light for diffuse reflectance. This may be accomplished by, e.g., using a fiber switch, or a beam splitter or dichroic beam combiner with focusing optics. Alternatively, separate fibers may be used for providing fluorescence excitation light and light for diffuse reflectance measurements.

To perform spectroscopy, the acquired spectra may be fitted using a custom made Matlab 7.9.0 (Mathworks, Natick, Mass.) algorithm. In this algorithm, a widely accepted analytical model was implemented, namely the model introduced by the reference T. J. Farrel, M. S. Patterson and B. C. Wilson, "A diffusion theory model of spatially resolved, steady-state diffuse reflectance for the non-invasive determination of tissue optical properties", Med. Phys. 19 (1992) p. 879-888, which is hereby incorporated by reference in entirety. The input arguments for the model of this reference are the absorption coefficient $\mu_a(\lambda)$, the reduced scattering coefficient $\mu'_s(\lambda)$ and the center-to-center distance between the emitting and collecting fibers at the tip of the probe.

In the following part, the model will be explained briefly. The used formulas are mainly based on work of Nachabé et al., and reference is thus made to R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442, which is hereby incorporated by reference in entirety, and furthermore reference is made to R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010), which is also hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter a corresponds to the reduced scattering amplitude at this specific wavelength.

$$\mu_s(\lambda) = a\left(\rho_{MR}\left(\frac{\lambda}{\lambda_0}\right)^{-b} + (1-\rho_{MR})\left(\frac{\lambda}{\lambda_0}\right)^{-4}\right)[\text{cm}^{-1}] \quad \text{(Eq. 1)}$$

Figure 8:
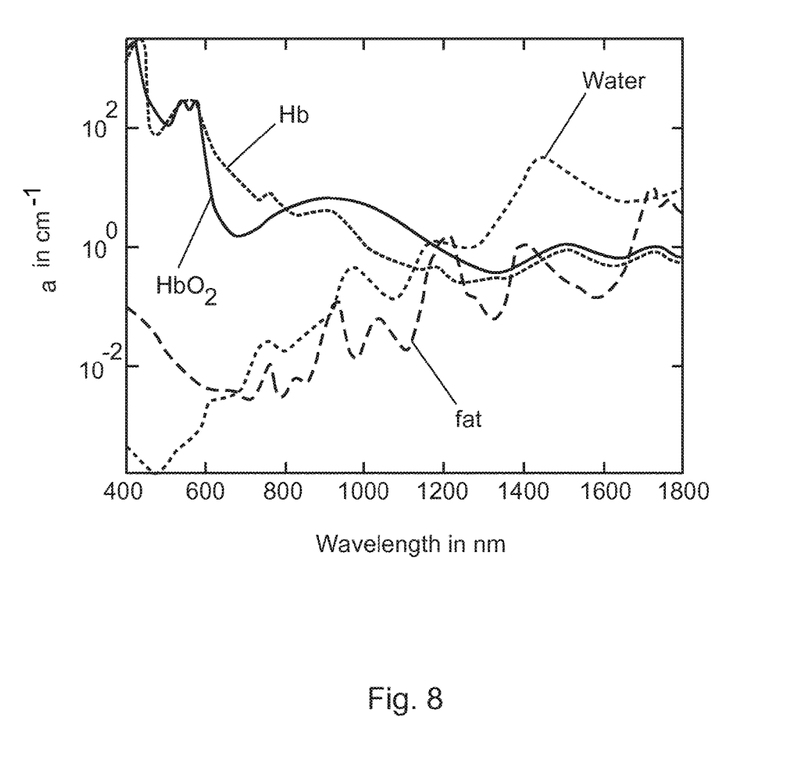
FIG. 8 shows a log plot of absorption coefficient of blood, water and fat.

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size. For a homogeneous distribution of absorbers, the total light absorption coefficient $\mu_a(\lambda)$ can be computed as products of the extinction coefficients and volume fraction of the absorbers (see FIG. 8)

$$\mu_a^{Total} = f_1\mu_a^1 + f_2\mu_a^2 + f_3\mu_a^3 + \quad \text{(Eq. 2)}$$

Instead of modeling the absorption coefficient $\mu_a(\lambda)$ as the sum of absorption coefficients weighted by the respective concentrations of the four chromophores of interest, it was decided to express the tissue absorption coefficient as $$\mu_a^{Tissue}(\lambda) = C(\lambda)\nu_{Blood}\mu_a^{Blood}(\lambda) + \nu_{WL}\mu_a^{WL}(\lambda)[\text{cm}^{-1}] \quad \text{(Eq. 3)}$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL}=[Lipid]+[H_2O]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1-\exp(-2R\mu_a^{Blood}(\lambda))}{2R\mu_a^{Blood}(\lambda)} \quad \text{(Eq. 4)}$$

where R denotes the average vessel radius expressed in cm. The absorption coefficient related to blood is given by $$\mu_a^{Blood}(\lambda)=\alpha_{BL}\mu_a^{HbO_2}(\lambda)+(1-\alpha_{BL})\mu_a^{Hb}(\lambda)[\text{cm}^{-1}] \quad \text{(Eq. 5)}$$

where $\mu_a^{HbO_2}(\lambda)$ and $\lambda_a^{Hb}(\lambda)$ represent the basic extinction coefficient spectra of oxygenated hemoglobin HbO$_2$ and deoxygenated hemoglobin Hb, respectively. The oxygenated hemoglobin fraction in the total amount of hemoglobin is noted $\alpha_{BL}=[HbO_2]/[HbO_2]+[Hb])$ and is commonly known as the blood oxygen saturation. The absorption due to the presence of water and lipid in the measured tissue is defined as $$\mu_a^{WL}(\lambda)=\alpha^{WL}\mu_a^{Lipid}(\lambda)+(1-\alpha_{WL})\mu_a^{H_2O}(\lambda)[\text{cm}^{-1}] \quad \text{(Eq. 6)}$$

In this case the concentration of lipid related to the total concentration of lipid and water together can be written as $\alpha_{WF}=[Lipid]/([Lipid]+[H_2O])$, where [Lipid] and [H$_2$O] correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf. the reference R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442. For further explanation and validation of this theorem reference is made to the reference R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For example by means of the described algorithm optical tissue properties may be derived such as the scattering coefficient and absorption coefficient of different tissue chromophores: e.g. hemoglobin, oxygenated hemoglobin, water, fat etc. These properties are different between normal healthy tissue and diseased (cancerous) tissue.

The main absorbing constituents in normal tissue dominating the absorption in the visible and near-infrared range are blood (i.e. hemoglobin), water and fat. In FIG. 8 the absorption coefficient of these chromophores as a function of the wavelength are presented. Note that blood dominates the absorption in the visible range, while water and fat dominate in the near infrared range.

The total absorption coefficient is a linear combination of the absorption coefficients of for instance blood, water and fat (hence for each component the value of that shown in FIG. 8 multiplied by its volume fraction). By fitting the model to the measurement while using the power law for scattering, the volume fractions of the blood, water and fat as well as the scattering coefficient may be determined.

The needles according to the invention can be used in minimally invasive needle interventions such as low-back pain interventions or taking biopsies in the field of cancer diagnosis or in case where tissue characterization around the needle is required.

In the following, exemplary needles according to the invention will be described with respect to their outer diameter, their insertion length, and their preferred use.

A biopsy needle might have an outer diameter of 1.27 mm up to 2.108 mm, might be inserted into tissue with 100 mm to 150 mm of its length, and might be used in soft tissue core biopsies in the neck, the head, the breast, the prostate, and the liver.

A fine aspiration needle of soft tissue might have an outer diameter between 0.711 mm and 2.108 mm, might be inserted into soft tissue with 100 mm to 150 mm of its length, and might be used for aspiration of soft tissue.

A brain biopsy needle might have an outer diameter of 2.108 mm, might be inserted into tissue with 150 mm up to 250 mm of its length, and might be used for diagnostic brain biopsies.

Finally, the device may include a needle electrode having an outer diameter of 2.108 mm and smaller, the electrode might be inserted into tissue up to 250 mm of its length, and might be used for radio frequency ablation for instance of tumors.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 shaft
20 recess
30 bevel
40 optical fiber
45 fiber distance
50 tubular member
55 distal edge
60 console
64 light source
66 light detector 68 monitor
100 needle
110 optical fiber
120 fiber distance
200 needle
230 notch
$N_1$, $N_2$ normal vector

The invention claimed is:

1. A biopsy device comprising:
a shaft; and
a tubular member, the shaft being movably accommodated within the tubular member, and the shaft having a centered longitudinal axis and a distal end,
wherein a bevel is formed at the distal end of the shaft, the bevel facing upwardly,
wherein at least two channels are formed within the shaft in a longitudinal direction of the shaft, each channel forming an opening in a surface of the bevel, wherein an optical fiber is accommodated within each of the channels,
wherein a recess is formed in the shaft adjacent the distal end of the shaft, the recess facing sidewardly;
wherein upwardly and sidewardly are directions that are mutually offset in a circumferential direction about the longitudinal axis of the shaft, and
wherein the at least two channels are included in a plane that is laterally offset from the centered longitudinal axis in a direction away from a side of the shaft in which the recess is formed.

2. The biopsy device of claim 1, wherein a distance between two openings in the bevel surface of the at least two channels is greater than a diameter of the shaft.

3. The biopsy device of claim 1, wherein the recess is formed relative to the bevel with an offset of at least 45 degree in the circumferential direction of the shaft.

4. The biopsy device of claim 1, wherein the recess is formed relative to the bevel with an offset of 90 degree in the circumferential direction of the shaft.

5. The biopsy device of claim 1, wherein the shaft is movable between a first position in which the recess is covered by the tubular member and a second position in which the recess is not covered by the tubular member.

6. The biopsy device of claim 1, wherein the tubular member includes a sharpened distal edge.

7. The biopsy device of claim 1, wherein the recess is adapted to accommodate a tissue sample to be taken from a tissue.

8. The biopsy device of claim 1, further comprising a console including a light source, a light detector and a processing unit for processing signals provided by the light detector.

9. The biopsy device of claim 8, wherein one of the light source and light detector provides wavelength selectivity.

10. The biopsy device of claim 8, wherein the light source is one of a laser, a light-emitting diode or a filtered light source.

11. The biopsy device of claim 8, wherein the console further comprises one of a fiber switch, a beam splitter or a dichroic beam combiner.

12. The biopsy device of claim 8, wherein the console is adapted to perform a process selected from the group consisting of diffuse reflectance spectroscopy, diffuse optical tomography, differential path length spectroscopy, and Raman spectroscopy.

13. The biopsy device of claim 8, wherein the console further comprises a monitor.

14. A biopsy device comprising:
a tubular member; and
a shaft movably accommodated within the tubular member, the shaft comprising:
a centered longitudinal axis;
a bevel at a distal end of the shaft, the a surface of the bevel facing upwardly;
a recess in the shaft adjacent the distal end of the shaft, the recess having a bottom surface and facing sidewardly, wherein upwardly and sidewardly are directions that are mutually offset in a circumferential direction about the centered longitudinal axis of the shaft; and
two channels formed in a longitudinal direction within the shaft, the two channels having corresponding openings in the bevel surface, and accommodating optical fibers, respectively,
wherein the two channels are in a plane laterally offset from the centered longitudinal axis in a direction away from the bottom surface of the recess.

15. The biopsy device of claim 14, wherein the recess has a depth in the shaft of approximately half a diameter of the shaft.

16. The biopsy device of claim 14, wherein the corresponding openings of the two channels in the bevel surface are aligned and offset from a center line of the bevel.

17. A shaft movably accommodated within a tubular member of a biopsy device, the shaft comprising:
a bevel at a distal end of the shaft, a bevel surface of the bevel facing a first direction;
a recess adjacent the distal end of the shaft, a recess surface of the recess facing a second direction that is circumferentially offset from the first direction about a longitudinal axis of the shaft; and
a plurality of channels within the shaft formed in a longitudinal direction and containing optical fibers, respectively, the plurality of channels having a corresponding plurality of openings in the bevel surface,
wherein the plurality of channels are included in a plane arranged in parallel and at a non-zero-distance from another plane including the longitudinal shaft axis of the shaft and a an intersecting normal vector of the bevel.

* * * * *